United States Patent
Valdastri et al.

(10) Patent No.: US 9,737,364 B2
(45) Date of Patent: Aug. 22, 2017

(54) LOCAL MAGNETIC ACTUATION OF SURGICAL DEVICES

(71) Applicant: Vanderbilt University, Nashville, TN (US)

(72) Inventors: Pietro Valdastri, Nashville, TN (US); Alan J. Herline, Brentwood, TN (US); Christian Di Natali, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 960 days.

(21) Appl. No.: 13/893,611

(22) Filed: May 14, 2013

(65) Prior Publication Data
US 2013/0298715 A1 Nov. 14, 2013

Related U.S. Application Data

(60) Provisional application No. 61/646,531, filed on May 14, 2012.

(51) Int. Cl.
*A61B 34/00* (2016.01)
*A61B 19/00* (2006.01)
(Continued)

(52) U.S. Cl.
CPC .............. *A61B 19/22* (2013.01); *A61B 17/29* (2013.01); *A61B 34/70* (2016.02); *A61B 34/73* (2016.02);
(Continued)

(58) Field of Classification Search
CPC ................ A61B 1/00158; A61B 19/22; A61B 2017/2902; A61B 2017/2908;
(Continued)

(56) References Cited

U.S. PATENT DOCUMENTS 3,315,660 A 4/1967 Abella
3,858,572 A 1/1975 Binard et al.
(Continued)

FOREIGN PATENT DOCUMENTS

DE 102006019419 11/2007
EP 2163206 3/2010
(Continued)

OTHER PUBLICATIONS

PCT International Search Report and Written Opinion for Application No. PCT/US2015/049142 dated Dec. 11, 2015.
(Continued)

*Primary Examiner* — Charles A Marmor, II
*Assistant Examiner* — Carrie R Dorna
(74) *Attorney, Agent, or Firm* — Michael Best & Friedrich LLP

(57) ABSTRACT

A method of actuating a surgical device is described. A surgical tool is inserted into a body cavity of a patient through a natural orifice. A distal end of an actuation tool is inserted through a surgical access port in the body of the patient. The distal end of the actuation tool is positioned proximal to an external wall of the body cavity opposite the surgical tool. A magnetic coupling is established between the distal end of the actuation tool and the surgical tool. When the magnetic coupling is established, distal end of the actuation tool is located at the external wall of the body cavity and the surgical tool is located at the internal wall of the body cavity. The surgical tool is manipulated using the actuation tool through the magnetic coupling.

17 Claims, 6 Drawing Sheets

(51) Int. Cl.
*A61B 17/29* (2006.01)
*A61B 17/00* (2006.01)

(52) U.S. Cl.
CPC ............... *A61B 2017/00876* (2013.01); *Y10T 74/20396* (2015.01)

(58) Field of Classification Search
CPC .... A61B 2019/2215; A61B 2019/2219; A61B 2019/2253
See application file for complete search history.

(56) References Cited

U.S. PATENT DOCUMENTS

| | | | |
|---|---|---|---|
| 3,870,072 | A | 3/1975 | Lindemann |
| 4,048,992 | A | 9/1977 | Lindemann et al. |
| 4,207,887 | A | 6/1980 | Hiltebrandt et al. |
| 5,330,486 | A * | 7/1994 | Wilk ............. A61B 17/068 227/179.1 |
| 5,489,256 | A | 2/1996 | Adair |
| 6,248,080 | B1 | 6/2001 | Miesel et al. |
| 6,270,787 | B1 | 8/2001 | Ayer |
| 6,802,811 | B1 | 10/2004 | Slepian |
| 7,722,559 | B2 | 5/2010 | Uesugi et al. |
| 2001/0051766 | A1 | 12/2001 | Gazdzinski |
| 2003/0114731 | A1 | 6/2003 | Cadeddu et al. |
| 2005/0277852 | A1 | 12/2005 | Shih et al. |
| 2008/0015413 | A1 | 1/2008 | Barlow et al. |
| 2008/0021334 | A1 | 1/2008 | Finburgh et al. |
| 2008/0058835 | A1 | 3/2008 | Farritor et al. |
| 2008/0154093 | A1 | 6/2008 | Cho et al. |
| 2008/0207999 | A1 | 8/2008 | Abraham-Fuchs et al. |
| 2009/0054877 | A1 | 2/2009 | Hood et al. |
| 2009/0054909 | A1* | 2/2009 | Farritor .................. A61B 19/22 606/130 |
| 2009/0171268 | A1 | 7/2009 | Williams, Jr. et al. |
| 2009/0171373 | A1 | 7/2009 | Farritor et al. |
| 2009/0292205 | A1 | 11/2009 | Osaka |
| 2010/0100117 | A1 | 4/2010 | Brister et al. |
| 2010/0198008 | A1 | 8/2010 | Kawano |
| 2010/0256636 | A1 | 10/2010 | Fernandez et al. |
| 2011/0184235 | A1 | 7/2011 | Schostek et al. |
| 2011/0202070 | A1 | 8/2011 | Dario et al. |
| 2011/0301497 | A1 | 12/2011 | Shachar et al. |
| 2011/0313415 | A1 | 12/2011 | Fernandez et al. |
| 2012/0035416 | A1 | 2/2012 | Fernandez et al. |
| 2012/0041345 | A1 | 2/2012 | Rajamani et al. |
| 2012/0149981 | A1 | 6/2012 | Khait et al. |
| 2012/0271555 | A1 | 10/2012 | Levental et al. |
| 2013/0131695 | A1 | 5/2013 | Scarfogliero et al. |
| 2013/0165859 | A1 | 6/2013 | Imran |
| 2013/0225922 | A1 | 8/2013 | Schentag et al. |
| 2013/0298715 | A1 | 11/2013 | Valdastri et al. |
| 2013/0324914 | A1 | 12/2013 | Valdastri et al. |

FOREIGN PATENT DOCUMENTS

| | | |
|---|---|---|
| EP | 2286756 | 2/2011 |
| WO | 0030548 | 6/2000 |
| WO | 2004041068 | 5/2004 |
| WO | 2007013059 | 2/2007 |
| WO | 2007146987 | 12/2007 |
| WO | 2008122997 | 10/2008 |
| WO | 2009014917 | 1/2009 |
| WO | 2010042611 | 4/2010 |
| WO | 2010044053 | 4/2010 |
| WO | 2010046823 | 4/2010 |
| WO | 2011058505 | 5/2011 |
| WO | 2011135503 | 11/2011 |
| WO | 2012028557 | 3/2012 |
| WO | 2012035157 | 3/2012 |
| WO | 2012080947 | 6/2012 |
| WO | 2012164517 | 12/2012 |
| WO | 2013027182 | 2/2013 |

OTHER PUBLICATIONS

F. Carpi, N. Kastelein, M.Talcott, and C.Pappone. Magnetically controllable gastrointestinal steering ofvideo capsules. IEEE Transactions on Biomedical Engineering, 58:231-234, 2011.
J. Keller, C. Fibbe, F. Volke, J. Gerber, A. C. Mosse, M. Reimann-Zawadzki, E Rabinovitz, P. Layer,D. S. and V. Andresen, U. Rosien, and P. Swain. Inspection of the human stomach using remote controlled capsule endoscopy: a feasibility study in healthy volunteers. Gastrointestinal Endoscopy,73:22-28, 2011.
S. Park, R. Bergs, R. Eberhart, L. Baker, R. Fernandez, and J. Cadeddu. Trocar-less instrumentation forlaparoscopy: magnetic positioning of intra-abdominal camera and retractor. Annals of Surgery,245:379-384, 2007.
J. F. Rey, H. Ogata, N. Hosoe, K. Ohtsuka, N. Ogata, K. Ikeda, H. Aihara, I. Pangtay, T. Hibi, S. Kudo,and H. Tajiri. Feasibility of stomach exploration with a guided capsule endoscope. Endoscopy, 42:541-545, 2010.
P. Swain, R. Austin, K. Bally, and R. Trusty. Development and testing of a tethered, independentcamera for NOTES and single-site laparoscopic procedures. Surgical Endoscopy, 24:2013-2021, 2010.
P. Valdastri, G. Ciuti, A. Verbeni, A. Menciassi, P. Dario, A. Arezzo, M. Morino. Magnetic air capsulerobotic system: Proof of concept of a novel approach for painless colonoscopy. Surgical Endoscopy,2011, in press.
A. Fritscher-Ravens, S. Fox, C.P. Swain, P. Mills, and G. Long. Cathcam guide wire-directedcolonoscopy: first pilot study in patients with a previous incomplete colonoscopy. Endoscopy, 38:209-213, 2006.
B. Vucelic, D. Rex, R. Pulanic, J. Pfefer, I. Hrstic, B. Levin, Z. Halpern, and N. Arber. The Aer-o-Scope: proof of concept of a pneumatic, skill-independent, self-propelling, self-navigating colonoscope.Gastroenterology, 130:672-677, 2006.
F. Cosentino, E. Tumino, G.R. Passoni, E. Morandi, and A. Capria. Functional evaluation of theEndotics System, a new disposable self-propelled robotic colonoscope: in vitro tests and clinical trial. International Journal of Artificial Organs, 32:517-527, 2009.
M. Shike, Z. Fireman, R. Eliakim, O. Segol, A. Sloyer, L.B. Cohen, S. Goldfarb-Albak, and A. Repici.Sightline Colonosight system for a disposable, power-assisted, non-fiber-optic colonoscopy.Gastrointestinal Endoscopy, 68:701-710, 2008.
T. Rösch, A. Adler, H. Pohl, E. Wettschureck, M. Koch, B. Wiedenmann, and N. Hoepner. A motor-driven single-use colonoscope controlled with a hand-held device: a feasibility study involunteers. Gastrointestinal Endoscopy, 67:1139-1146, 2008.
A. Eickhoff, J. Van Dam, R. Jakobs, V. Kudis, D. Hartmann, U. Damian, U. Weickert, D. Schilling, andJ.F. Riemann. Computer-assisted colonoscopy (the NeoGuide endoscopy system): results of the firsthuman clinical trial (pace study). The American Journal of Gastroenterology, 102:261-266, 2007.
M. Moshkowitz, Y. Hirsch, I. Carmel, T. Duvdevany, I. Fabian, E.P. Willenz, and J. Cohen. A noveldevice for rapid cleaning of poorly prepared colons. Endoscopy, 42:834-836, 2010.
A. Fritscher-Ravens, C. Mosse, T. Mills, K. Ikeda, P. Swain, Colon cleaning during colonoscopy: a newmechanical cleaning device tested in a porcine model. Gastrointestinal Endoscopy, 63:141-143, 2006.
H. Richert, B. Hilgenfeld, and P. Gomert, "Magnetic sensor techniques for new intelligent endoscopic capsules," http://www.vector-project.com/press/artikel/VECTOR%20article_Richert_MagneticSensorTechniques.pdf, publicly available prior to Sep. 17, 2012.
Than, T. D.; Alici, G.; Zhou, H ; Li, W.; , "A Review of Localization Systems for Robotic Endoscopic Capsules," Biomedical Engineering, IEEE Transactions on , vol.59, No. 9, pp. 2387-2399, Sep. 2012.
NDI Medical's Aurora product, http://www.ndigital.com/medical/products/aurora/, publicly available prior to Sep. 17, 2012.
M. B. H. Gerald Rogers. The safety of carbon dioxide insufflation during colonoscopic electro-surgical polypectomy. Gastrointestinal Endoscopy, 20:115-117, 1974.

(56) References Cited

OTHER PUBLICATIONS

P. E J.-M. D. Filip Janssens, Jacques Deviere. Carbon dioxide for gut distension duringdigestive endoscopy: Technique and practice survey. World Journal of Gastroenterology, 15(12):1475-1479, 2009.

F. A. Macrae, K. G. Tan, and C. B. Williams. Towards safer colonoscopy: a report on thecomplications of 5000 diagnostic or therapeutic colonoscopies. Gut, 24(5):376{383, 1983.

W. J. R. P. Phaosawasdi K, Cooley W. Carbon dioxide-insufflated colonoscopy: an ignoredsuperior technique. Gastrointestinal Endoscopy, 32:330-333, 1986.

K. Sumanac, I. Zealley, B. M. Fox, J. Rawlinson, B. Salena, J. K. Marshall, G. W. Stevenson,and R. H. Hunt. Minimizing postcolonoscopy abdominal pain by using fCO2g insufflation: Aprospective, randomized, double blind, Controlled trial evaluating a new commercially availablefCO2g delivery system. Gastrointestinal Endoscopy, 56(2):190-194, 2002.

J. C. H. Wong, K. K. Yau, H. Y. S. Cheung, D. C. T. Wong, C. C. Chung, and M. K W. Li.Towards painless colonoscopy: A randomized controlled trial on carbon dioxide-insufflatingcolonoscopy. ANZ Journal of Surgery, 78 (10):871-874, 2008.

PCT International Search Report and Written Opinion for Application No. PCT/US2014/012086 dated May 14, 2014.

PCT International Search Report and Written Opinion for Application No. PCT/IB2012/052739 dated Aug. 7, 2012.

"S. Best, E. Olweny, S. Park, P. Smith, R. Fernandez, D. Scott, R. Bergs, and J. Cadeddu. Newgeneration magnetic camera facilitates porcine LESS nephrectomy. The Journal of Urology, 185:e413-e413, 2011.".

P. Valdastri, C. Quaglia, E. Susilo, A. Menciassi, P. Dario, C.N. Ho, G. Anhoeck, M.O. Schurr, "Wireless Therapeutic Endoscopic Capsule: in-vivo Experiment", Endoscopy, 2008, vol. 40, pp. 979-982.

P. Valdastri, A. Menciassi, P. Dario, "Transmission Power Requirements for Novel ZigBee Implants in the Gastrointestinal Tract", IEEE Transactions on Biomedical Engineering, 2008, vol. 55, No. 6, pp. 1705-1710.

P. Valdastri, S. Rossi, A. Menciassi, V. Lionetti, F. Bernini, F. A. Recchia, P. Dario, "An Implantable ZigBee Ready Telemetric Platform for in Vivo Monitoring of Physiological Parameters", Sensors and Actuators A: Physical, 2008, vol. 142, No. 1, pp. 369-378.

A. Sieber, P. Valdastri, K. Houston, C. Eder, O. Tonet, A. Menciassi, P. Dario, "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.

A. Sieber, P. Valdastri, K. Houston, A. Menciassi, P. Dario, "Flip Chip Microassembly of a Silicon Triaxial Force Sensor on Flexible Substrates", Sensors and Actuators A: Physical, 2008, vol. 142, No. 1, pp. 421-428.

L. Beccai, S. Roccella, L. Ascari, P. Valdastri, A. Sieber, M. C. Carrozza, P. Dario, "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168. [.

C. Oddo, P. Valdastri, L. Beccai, S. Roccella, M.C. Carrozza, P. Dario, "Investigation on calibration methods for multi-axis, linear and redundant force sensors", Measurement Science and Technology, 2007, vol. 18, pp. 623-631.

P. Valdastri, K. Houston, A. Menciassi, P. Dario, A. Sieber, M. Yanagihara, M. Fujie, "Miniaturised Cutting Tool with Triaxial Force Sensing Capabilities for Minimally Invasive Surgery", ASME Journal of Medical Devices, 2007, vol. 1, N. 3, pp. 206-211.

G. Turchetti, B. Labella, P. Valdastri, A. Menciassi, P. Dario, "The importance of giving an alternative: the case of fetal surgery", Int. J. Healthcare Technology and Management, 2007, vol. 8, Nos. 3-4, pp. 250-267.

P. Valdastri, K. Harada, A. Menciassi, L. Beccai, C. Stefanini, M. Fujie, and P. Dario, "Integration of a Miniaturised Triaxial Force Sensor in a Minimally Invasive Surgical Tool", IEEE Transactions on Biomedical Engineering, 2006, vol. 53, No. 11, 2397-2400.

P. Valdastri, P. Corradi, A. Menciassi, T. Schmickl, K. Crailsheim, J. Seyfried, P. Dario, "Micromanipulation, Communication and Swarm Intelligence Issues in a Swarm Microrobotic Platform", Robotics and Autonomous Systems, 2006, vol. 54, No. 10, pp. 789-804.

P. Valdastri, S. Roccella, L. Beccai, E. Cattin, A. Menciassi, M. C. Carrozza, P. Dario, "Characterization of a novel hybrid silicon three-axial force sensor", Sensors and Actuators A: Physical, 2005, vol. 123-124C, pp. 249-257.

L. Beccai, S. Roccella, A. Arena, F. Valvo, P. Valdastri, A. Menciassi, M. C. Carrozza, P. Dario, "Design and fabrication of a hybrid silicon three axial force sensor for biomechanical applications", Sensors and Actuators A: Physical, 2005, vol. 120, No. 2, pp. 370-382.

P. Valdastri, A. Menciassi, A. Arena, C. Caccamo, and P. Dario, "An Implantable Telemetry Platform System for in vivo Monitoring of Physiological Parameters", IEEE Transactions on Information Technology in Biomedicine, 2004, vol. 8, No. 3, pp. 271-278.

X. Wang, C. Di Natali, M. Beccani, M. Kern, P. Valdastri, M. Rentschler, "Novel Medical Wired Palpation Device: A Device Validation Study of Material Properties", Transducers 2013, Barcelona, Spain, pp. 1653-1658.

M. Beccani, C. Di Natali, M. E. Rentschler, P. Valdastri, "Wireless Tissue Palpation: Proof of Concept for a Single Degree of Freedom", IEEE International Conference on Robotics and Automation (ICRA) 2013, Karlsruhe, Germany, pp. 703-709.

M. Beccani, C. Di Natali, M. Rentschler, P. Valdastri, "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).

C. Di Natali, P. Valdastri "Remote active magnetic actuation for a single-access surgical robotic manipulator", in Proc of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.

C. Di Natali, T. Ranzani, M. Simi, A. Menciassi, P. Valdastri "Trans-abdominal Active Magnetic Linkage for Robotic Surgery: Concept Definition and Model Assessment", in Proc. of IEEE International Conference on Robotics and Automation (ICRA) 2012, St Paul, MN, USA, May 2012, pp. 695-700.

M. Simi, G. Gerboni, A. Menciassi, P. Valdastri, "Magnetic Mechanism for Wireless Capsule Biopsy", in Proc. of ASME Design of Medical Devices Conference, Apr. 10-12, 2012, Minneapolis, MN, ASME Journal of Medical Devices, vol. 6, p. 017611-1.

T. Ranzani, C. Di Natali, M. Simi, A. Menciassi, P. Dario, P. Valdastri, "A Novel Surgical Robotic Platform Minimizing Access Trauma", in Proc. of 4th Hamlyn Symposium on Medical Robotics, London, UK, Jun. 2011, pp. 15-16.

P. Valdastri, G. Ciuti, A. Verbeni, A. Menciassi, P. Dario, A. Arezzo, M. Morino, "Magnetic air capsule robotic system: a novel approach for painless colonoscopy", 19th International Congress of the European Association of Endoscopic Surgery (EAES) in Turin, Italy.

M. Simi, G. Sardi, P. Valdastri, A. Menciassi, P. Dario, "Magnetic Levitation Camera Robot for Endoscopic Surgery", in Proc. of IEEE International Conference on Robotics and Automation (ICRA) 2011, Shanghai, China, May 2011, pp. 5279-5284.

O. Alonso, J. Canals, L. Freixas, J. Samitier, A. Dieguez, M. Vatteroni, E. Susilo, C. Cavallotti, P. Valdastri, "Enabling multiple robotic functions in an endoscopic capsule for the entire gastrointestinal tract exploration", in Proc. ESSCIRC, 2010, pp. 386-389.

J. L. Toennies, G. Ciuti, B. F. Smith, A. Menciassi, P. Valdastri, and Robert J. Webster III, "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.

G. Tortora, S. Caccavaro, P. Valdastri, A. Menciassi, P. Dario, "Design of an autonomous jellyfish miniature robot based on a novel concept of magnetic actuation", in Proc. of IEEE International

(56) References Cited

OTHER PUBLICATIONS

Conference on Robotics and Automation (ICRA) 2010, Anchorage, AK, USA, May 2010, pp. 1592-1597.
L. S. Chiang, P. S. Jay, P. Valdastri, A. Menciassi, P. Dario, "Tendon Sheath Analysis for Prediction of Distal End Force and Elongation", in Proc. IEEE/ASME Conference on Advanced Intelligent Mechatronics 2009, Singapore, Jul. 2009, pp. 332-337.
O. Tonet, M. Marinelli, G. Megali, A. Sieber, P. Valdastri, A. Menciassi, P. Dario, "Control of a teleoperated nanomanipulator with time delay under direct vision feedback", in Proc. of IEEE International Conference on Robotics and Automation (ICRA) 2007, Rome, Italy, Apr. 2007, pp. 3514-3519.
J. L. Toennies, R. J. Webster III, P. Valdastri, "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).
A. Menciassi, P. Valdastri, K. Harada, P. Dario, "Single and Multiple Robotic Capsules for Endoluminal Diagonosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 978-1-4419-1125-4.
B. Laulicht, N. Gidmark, A. Tripathl, E. Mathiowitz, "Localization of magnetic pills," Proc. of the National Academy of Sciences, vol. 108, No. 6, 2252-2257 (Feb. 8, 2011).
PCT International Search Report and Written Opinion for Application No. PCT/EP2011/064764 dated Oct. 10, 2011.
Toennies, J.L. et al., "A Wireless Insufflation System for Capsular Endoscopes," Journal of Medical Devices, vol. 3 (Jun. 2009).
Toennies, Jenna L. et al., "Initial Feasibility Studies on Wireless Insufflation of the GI Tract," IEEE International Conference on Robotics and Automation 2010—Workshop on Meso-ScaleRobotics for Medical Interventions, (May 3, 2010).
Smith, Byron, "Wireless Insufflation for Wireless Capsule Endoscopy," Vanderbilt University Master's Thesis (Aug. 2012).
Pedersen, Amanda, "Capsule Endoscopy in ER Could Drop Admission Rate," Medical Device Daily (Feb. 13, 2013).
PillCam Capsule Endoscopy products by Given Imaging, http://www.givenimaging.com/en-int/Innovative-Solutions/Capsule-Endoscopy/Pages/default.aspx, available prior to Sep. 17, 2012.
Lehman, A.C. et al., "Surgery with Cooperative Robots," Comput. Aided. Surg., 13(2), pp. 95-105 (Mar. 2008).
Cadeddu, J.A. et al., "Novel magnetically guided intra-abdominal camera to facilitate laparoendoscopic single site surgery: initial human experience," Surg. Endoscopy, 23, pp. 1984-1899 (May 9, 2009).
C. S. Bell, K. L. Obstein, P. Valdastri, "Image partitioning and illumination in image-based pose detection for teleoperated flexible endoscopes", Artificial Intelligence in Medicine, 2013, in press.
M. Beccani, C. Di Natali, L. Sliker, J. Schoen, M. E. Rentschler, P. Valdastri, "Wireless Tissue Palpation for Intraoperative Detection of Lumps in Soft Tissue", IEEE Transactions on Biomedical Engineering, 2013, in press.
M. Simi, G. Gerboni, A. Menciassi, P. Valdastri, "Magnetic Torsion Spring Mechanism for a Wireless Biopsy Capsule", ASME Journal of Medical Devices, 2013, in press.
A. Arezzo, A. Menciassi, P. Valdastri, G. Ciuti, G. Lucarini, M. Salerno, C. Di Natali, M. Verra, P. Dario, M. Morino, "Experimental assessment of a novel robotically-driven endoscopic capsule compared to traditional colonoscopy", Digestive and Liver Disease, 2013, vol. 45, N. 8, pp. 657-662.
C. Di Natali, M. Beccani, P. Valdastri, "Real-Time Pose Detection for Magnetic Medical Devices", IEEE Transactions on Magnetics, 2013, vol. 49, N. 7, pp. 3524-3527.
M. Simi, R. Pickens, A. Menciassi, S. D. Herrell, P. Valdastri, "Fine tilt tuning of a laparoscopic camera by local magnetic actuation: Two-Port Nephrectomy Experience on Human Cadavers", Surgical Innovation, 2013, vol. 20, N. 4, pp. 385-394.
J. L. Gorlewicz, S. Battaglia, B. F. Smith, G. Ciuti, J. Gerding, A. Menciassi, K. L. Obstein, P. Valdastri, R. J. Webster III, "Wireless Insufflation of the Gastrointestinal Tract", IEEE Transactions on Biomedical Engineering, 2013, vol. 60, N. 5, pp. 1225-1233.
T. Horeman, D. D. Kurteva, P. Valdastri, F. W. Jansen, J. J. van den Dobbelsteen, J. Dankelman, "The Influence of Instrument Configuration on Tissue Handling Force in Laparoscopy", Surgical Innovation, 2013, vol. 20, N. 3, pp. 260-267.
M. Simi, M. Silvestri, C. Cavallotti, M. Vatteroni, P. Valdastri, A. Menciassi, P. Dario, "Magnetically Activated Stereoscopic Vision System for Laparoendoscopic Single Site Surgery", IEEE/ASME Transactions on Mechatronics, 2013, vol. 18, N. 3, pp. 1140-1151.
K. L. Obstein, S. Battaglia, B. F. Smith, J. S. Gerding, P. Valdastri, "Novel approach for colonic insufflation via an untethered capsule (with video)", Gastrointestinal Endoscopy, 2013, vol. 77, N. 3, pp. 516-517.
K. Obstein, P. Valdastri, "Advanced Endoscopic Technologies for Colorectal Cancer Screening", World Journal of Gastroenterology, 2013, vol. 19, N. 4, pp. 431-439.
P. Valdastri, M. Simi, R. J. Webster III, "Advanced Technologies for Gastrointestinal Endoscopy", Annual Review of Biomedical Engineering, 2012, vol. 14, pp. 397-429.
G. Ciuti, N. Pateromichelakis, M. Sfakiotakis, P. Valdastri, A. Menciassi, D. P. Tsakiris, P. Dario, "A wireless module for vibratory motor control and inertial sensing in capsule endoscopy", Sensors and Actuators A: Physical, 2012, vol. 186, pp. 270-276.
P. Valdastri, G. Ciuti, A. Verbeni, A. Menciassi, P. Dario, A. Arezzo, M. Morino, "Magnetic air capsule robotic system: Proof of concept of a novel approach for painless colonoscopy", Surgical Endoscopy, 2012, vol. 26, N. 5, pp. 1238-1246.
G. Ciuti, M. Salerno, G. Lucarini, P. Valdastri, A. Arezzo, A. Menciassi, M. Morino, P. Dario, "A Comparative Evaluation of Control Interfaces for a Robotic-Aided Endoscopic Capsule Platform", IEEE Transactions on Robotics, 2012, vol. 28, N. 2, pp. 534-538.
M. Simi, N. Tolou, P. Valdastri, J. L. Herder, A. Menciassi, P. Dario, "Modeling of a Compliant Joint in a Magnetic Levitation System for an Endoscopic Camera", Mechanical Sciences, 2012, vol. 3, pp. 5-14.
M. Salerno, G. Ciuti, G. Lucarini, R. Rizzo, P. Valdastri, A. Menciassi, A. Landi, P. Dario, "A discrete-time localization method for capsule endoscopy based on on-board magnetic sensing", Measurement Science and Technology, 2012, 23 015701 (10pp).
C. Cavallotti, P. Merlino, M. Vatteroni, P. Valdastri, A. Abramo, A. Menciassi, P. Dario, "An FPGA-based flexible demo-board for endoscopic capsule design optimization", Sensors and Actuators A: Physical, 2011, vol. 172, No. 1, pp. 301-307.
M. Silvestri, M. Simi, C. Cavallotti, M. Vatteroni, V. Ferrari, C. Freschi, P. Valdastri, A. Menciassi, P. Dario, "Comparative study on surgical performance between two- and three-dimensional vision systems and interfaces", Surgical Innovation, 2011, vol. 18, No. 3, pp. 223-230.
P. Valdastri, E. Sinibaldi, S. Caccavaro, G. Tortora, A. Menciassi, P. Dario, "A novel magnetic actuation system for miniature swimming robots", IEEE Transactions on Robotics, 2011, vol. 27, No. 4, pp. 769-779.
V. Pensabene, P. Valdastri, S. Tognarelli, A. Menciassi, A. Arezzo, P. Dario, "Mucoadhesive film for anchoring assistive surgical instruments in endoscopic surgery: in vivo assessment of deployment and attachment", Surgical Endoscopy, 2011, vol. 25, No. 9, pp. 3071-3079.
P. Valdastri, E. Susilo, T. Förster, C. Strohhöfer, A. Menciassi, P. Dario, "Wireless implantable electronic platform for chronic fluorescent-based biosensors", IEEE Transactions on Biomedical Engineering, 2011, vol. 58, No. 6, pp. 1846-1854.
M. Vatteroni, P. Valdastri, A. Sartori, A. Menciassi, P. Dario, "Linear-logarithmic CMOS pixel with tunable dynamic range", IEEE Transactions on Electron Devices, 2011, vol. 58, No. 4, pp. 1108-1115.
S. Tognarelli, V. Pensabene, S. Condino, P. Valdastri, A. Menciassi, A. Arezzo, P. Dario, "A pilot study on a new anchoring mechanism

(56) References Cited

OTHER PUBLICATIONS for surgical applications based on mucoadhesives", Minimally Invasive Therapy & Allied Technologies, 2011, vol. 20, No. 1, pp. 3-13.
M. Piccigallo, U. Scarfogliero, C. Quaglia, G. Petroni, P. Valdastri, A. Menciassi, P. Dario, "Design of a novel bimanual robotic system for single-port laparoscopy", IEEE/ASME Transactions on Mechatronics, 2010, vol. 15, No. 6, pp. 871-878.
M. Vatteroni D. Covi, C. Cavallotti, P. Valdastri, A. Menciassi, P. Dario, A. Sartori, "Smart optical CMOS sensor for endoluminal applications", Sensors and Actuators A: Physical, 2010, vol. 162, No. 2, pp. 297-303.
D. Covi, C. Cavallotti, M. Vatteroni, L. Clementel, P. Valdastri, A. Menciassi, P. Dario, A. Sartori, "Miniaturized digital camera system for disposable endoscopic applications", Sensors and Actuators A: Physical, 2010, vol. 162, No. 2, pp. 291-296.
E. Buselli, V. Pensabene, P. Castrataro, P. Valdastri, A. Menciassi, P. Dario, "Evaluation of friction enhancement through soft polymer micro-patterns in active capsule endoscopy", Measurement Science and Technologies, 2010, 21 105802 (7pp).
P. Valdastri, C. Quaglia, E. Buselli, A. Arezzo, N. Di Lorenzo, M. Morino, A. Menciassi, P. Dario, "A Magnetic Internal Mechanism for Camera Steering in Wireless Endoluminal Applications", Endoscopy, 2010, vol. 42, pp. 481-486.
J. L. Toennies, G. Tortora, M. Simi, P. Valdastri, R. J. Webster III, "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.
M. Simi, G. Ciuti, S. Tognarelli, P. Valdastri, A. Menciassi, P. Dario, "Magnetic link design for a robotic laparoscopic camera", Journal of Applied Physics, 2010, vol. 107, No. 9, pp. 09B302-09B302-3.
M. Simi, P. Valdastri, C. Quaglia, A. Menciassi, P. Dario, "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.
G. Ciuti, R. Donlin, P. Valdastri, A. Arezzo, A. Menciassi, M. Morino, P. Dario, "Robotic versus manual control in magnetic steering of an endoscopic capsule", Endoscopy, 2010, vol. 42, pp. 148-152.
G. Ciuti, P. Valdastri, A. Menciassi, P. Dario, "Robotic magnetic steering and locomotion of capsule endoscope for diagnostic and surgical endoluminal procedures", Robotica, 2010, vol. 28, No. 2, pp. 199-207.
R. Carta, G. Tortora, J. Thoné, B. Lenaerts, P. Valdastri, A. Menciassi, R. Puers, P. Dario, "Wireless powering for a self-propelled and steerable endoscopic capsule for stomach inspection", Biosensors and Bioelectronics, 2009, vol. 25, No. 4, pp. 845-851.
C. Quaglia, E. Buselli, R. J. Webster III, P. Valdastri, A. Menciassi, P. Dario, "An Endoscopic Capsule Robot: A Meso-Scale Engineering Case Study", Journal of Micromechanics and Microengineering, 2009, vol. 19, No. 10, 105007 (11pp).
G. Tortora, P. Valdastri, E. Susilo, A. Menciassi, P. Dario, F. Rieber, M. O. Schurr, "Propeller-based wireless device for active capsular endoscopy in the gastric district", Minimally Invasive Therapy & Allied Technologies, 2009, vol. 18, No. 5, pp. 280-290.
E. Susilo, P. Valdastri, A. Menciassi, P. Dario, "A Miniaturized Wireless Control Platform for Robotic Capsular Endoscopy Using Advanced Pseudokernel Approach", Sensors and Actuators A: Physical, 2009, vol. 156, No. 1, pp. 49-58.
C. Cavallotti, M. Piccigallo, E. Susilo, P. Valdastri, A. Menciassi, P. Dario, "An Integrated Vision System with Autofocus for Wireless Capsular Endoscopy", Sensors and Actuators A: Physical, 2009, vol. 156, No. 1, pp. 72-78.
P. Valdastri, R. J. Webster III, C. Quaglia, M. Quirini, A. Menciassi, P. Dario, "A New Mechanism for Meso-Scale Legged Locomotion in Compliant Tubular Environments", IEEE Transactions on Robotics, 2009, vol. 25, No. 5, pp. 1047-1057.
P. Valdastri, S. Tognarelli, A. Menciassi, P. Dario, "A scalable platform for biomechanical studies of tissue cutting forces", Measurement Science and Technology, 2009, vol. 20, 045801 (11pp).
E. Buselli, P. Valdastri, M. Quirini, A. Menciassi, P. Dario, "Superelastic leg design optimization for an endoscopic capsule with active locomotion", Smart Materials and Structures, 2009, vol. 18, 015001 (8pp).

\* cited by examiner

LOCAL MAGNETIC ACTUATION OF SURGICAL DEVICES

RELATED APPLICATIONS

This application claims the benefit of U.S. Provisional Patent Application No. 61/646,531, filed May 14, 2012 and entitled "LOCAL MAGNETIC ACTUATION," the entire contents of which are incorporated herein by reference.

BACKGROUND

The present invention relates to surgical devices as well as methods and mechanisms for actuating such surgical devices across a physical barrier.

SUMMARY

Embodiments of the invention provide mechanisms for remote magnetic actuation of surgical devices across a physical barrier. A surgical device is placed within the body of a patient (either surgically or through an existing orifice). The surgical device is magnetically actuated by an actuation tool positioned on the other side of a physical membrane from the surgical device. In some situations, the surgical device can be actuated by placing the actuation tool on the exterior skin of the patient. However, in some situations (particularly with obese patients), magnetic actuation of the device from the skin surface of the patient is not possible due to the thick layer of fat between the actuation tool and the surgical tool that is positioned within the body of the patient.

Some embodiments of the invention provide mechanisms and methods of magnetically actuating a surgical tool that are adapted to apply to obese patients. The platform includes a surgical tool, an actuation tool, and a magnetic coupling. The surgical tool is insertable into a body cavity of a patient—either through a natural orifice or surgically through an incision—and has at least one degree-of-freedom that is actuated by the actuation tool to perform an operative or auxiliary surgical function. The actuation tool is configured to be inserted into the body of a patient through a surgical access port and placed on the other side of a wall of the body cavity that contains the surgical tool. The magnetic coupling is established between the actuation tool and the surgical tool and transmits mechanical power (e.g., torque and rotational speed) through the physical barrier of the body cavity wall. The magnetic coupling includes magnets positioned within the actuation tool that are actively actuated externally and dual magnets positioned within the surgical tool. The dual magnets of the surgical tool move in response to the actuation of the magnets in the actuation tool. Furthermore, in some constructions, the magnetic couples—dually placed inside the actuation tool and the surgical tool—are used to anchor and stabilize the surgical tool.

In some embodiments, the surgical tool is introduced into a body cavity through a natural orifice, instead of a surgical access port, and the actuation tool is introduced into the patient's abdominal cavity (or other body cavity) through a surgical port. In some such embodiments, the source of mechanical power (i.e. the actuation tool) can reach deep inside the human body and be just few millimeters away from the surgical tool on the other side of the cavity walls (usually thinner than 1 cm). This enables an effective magnetic transmission of mechanical power across a physical barrier.

In some embodiments, the magnetic coupling includes a double 4-bar mechanical linkage inside the surgical tool that couples the movement of the magnets within the surgical tool with non-linear movement of the end effector (i.e., the actuatable mechanism of the surgical tool). This miniaturized mechanism, applied to the proposed local magnetic actuation, enables a force amplification of a factor of 6.

In some embodiments, the surgical tool includes at least one of a surgical camera with a steerable head, tissue retractors, cautery devices, surgical electrofrequency knives, laparoscopic graspers, and surgical pinching devices. The surgical tools can be used, for example, for (1) colorectal surgery, where the surgical tool is introduced into the colon through the anus and the actuation tool is introduced though a surgical abdominal port; (2) gastric surgery, where the surgical tool is introduced into the stomach through the mouth and the actuation tool is introduced though a surgical abdominal port; (3) urologic surgery, where the surgical tool is introduced through the urethra to reach the bladder and the actuation tool is introduced though a surgical abdominal port; (4) gynecologic surgery, where the surgical tool is introduced through the vagina to reach the uterus and the actuation tool is introduced though a surgical abdominal port; (5) lung surgery, where the surgical tool is introduced into the lungs through the nose or mouth and the actuation tool is introduced though a surgical thoracic port; and (6) bariatric surgery, where the surgical tool is introduced into the stomach through the mouth and the actuation tool is introduced though a surgical abdominal port.

In one embodiment, the invention provides a method of actuating a surgical device. A surgical tool is inserted into a body cavity of a patient through a natural orifice. A distal end of an actuation tool is inserted through a surgical access port in the body of the patient. The distal end of the actuation tool is positioned proximal to an external wall of the body cavity opposite the surgical tool. A magnetic coupling is established between the distal end of the actuation tool and the surgical tool. When the magnetic coupling is established, distal end of the actuation tool is located at the external wall of the body cavity and the surgical tool is located at the internal wall of the body cavity. The surgical tool is manipulated using the actuation tool through the magnetic coupling.

In another embodiment, the invention provides a surgical system including a surgical tool and an actuation tool. The surgical tool includes a first magnet. The actuation tool includes a handle and an actuation unit coupled to the handle by a rotational joint. The actuation unit also includes a second magnet. The first magnet of the surgical tool and the second magnet of the actuation tool form a magnetic coupling when the surgical tool is positioned proximal to an internal wall of the body cavity through a natural orifice and the actuation unit is positioned proximal to an exterior wall of the body cavity through a surgical access port. The surgical tool is configured to be manipulated by the actuation tool when magnetically coupled to the actuation unit.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
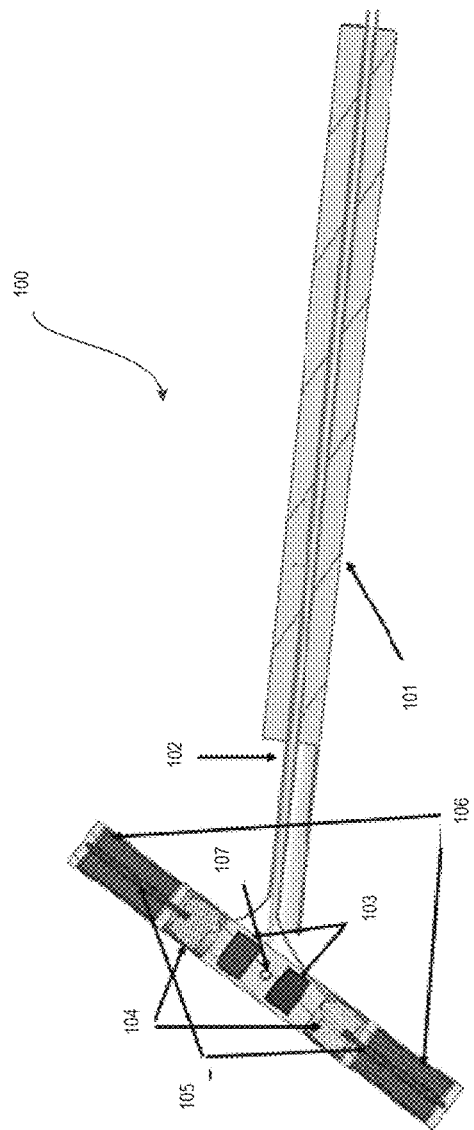
FIG. 1 is a cross-sectional view of an actuation tool according to one embodiment.

FIG. 1 illustrates an actuation tool 100 that controls the operation of a surgical device through a magnetic coupling. As described in further detail below, the surgical device is inserted into a body cavity while the distal end of the actuation tool 100 is positioned proximal to an external wall of the body cavity. The actuation tool 100 of FIG. 1 is configured and adapted to be inserted into the body of a patient through a surgical access port so that it can be positioned adjacent to the external wall of the body cavity to control the operation of the surgical device without interference or poor coupling due to the fat layers between the surface of the patient's skin and the body cavity that contains the surgical device.

The actuation tool 100 includes a handle 101 and a wire transmission linkage 102. The distal end of the actuation tool 100 includes a pair of anchoring magnets 103 and a mechanical transmission mechanism 104. Movement of the wire transmission linkage 102 either causes movement of the mechanism transmission mechanisms 104 or causes the mechanical transmission mechanisms 104 to perform an operation. In the example of FIG. 1, each mechanical transmission mechanisms 104 includes a shaft 105 that causes movement of an actuated magnet 106. The distal end of the actuation tool 100 also includes a rotational joint 107 that causes the distal end (including the actuated magnets 106) to move relative to the handle 101.

Figure 2:
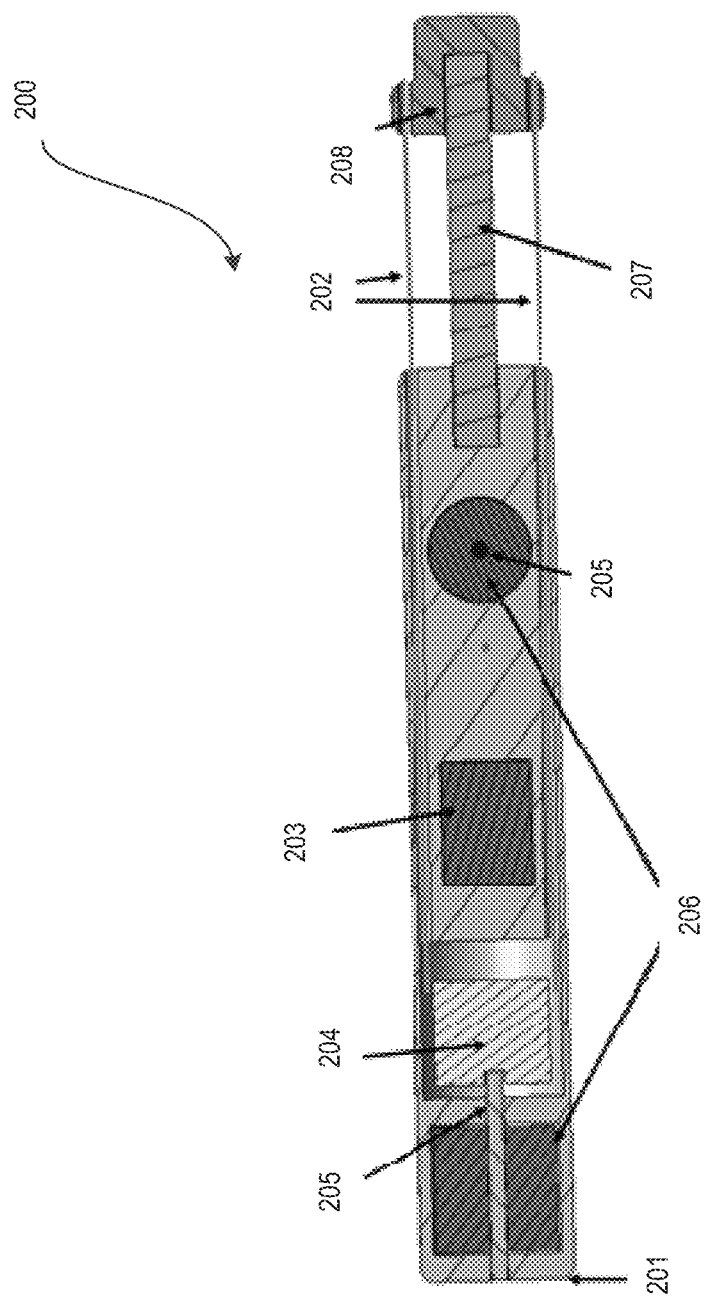
FIG. 2 is a cross-sectional view of a surgical tool that is magnetically actuated by the actuation tool of FIG. 1.

FIG. 2 illustrates a surgical device 200 that is controlled through a magnetic coupling with the actuation tool 100. The surgical device includes an instrument body 201 that houses a wire transmission linkage 202, an anchoring magnet 203, and a mechanical transmission mechanism 204. The instrument body 201 also houses a shaft 205 and one or more driven magnets 206. The anchoring magnet 203 of the surgical device 200 couples to the anchoring magnet 103 of the actuation tool 100 to control/restrict the movement of the surgical device within the body cavity of a patient. The driven magnets 206 are coupled to the actuated magnets 106 of the actuation tool 100 such that movement of the actuated magnets 106 causes a corresponding movement of the driven magnets 206. The movement of the driven magnets 206 causes movement and operation of components within the surgical device (including the mechanical transmission mechanism 204).

Figure 3:
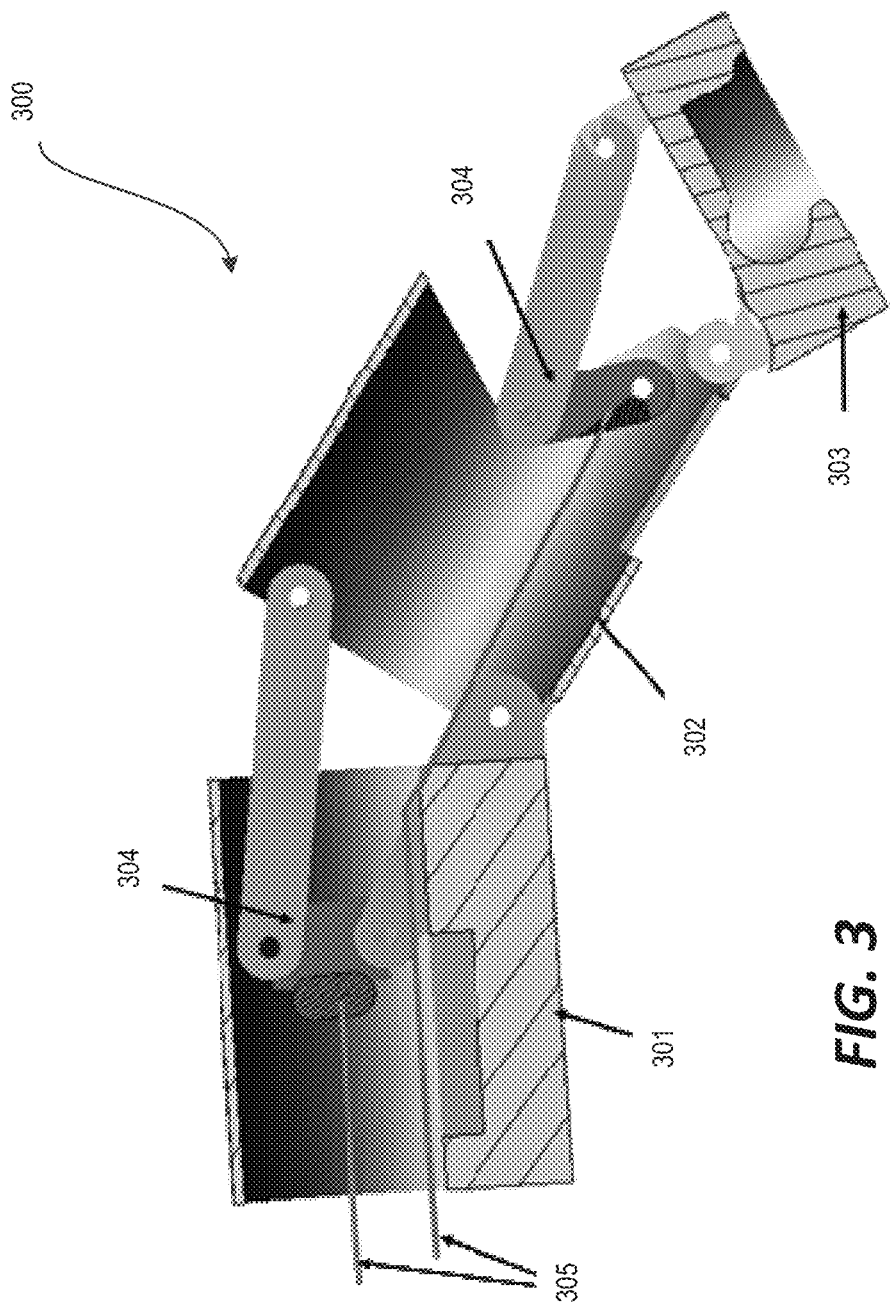
FIG. 3 is a cross-section view of a mechanical linkage used to manipulate the position of an end-effector of the surgical tool of FIG. 2.

More specifically, in the example of FIG. 2, actuation of the driven magnets 206 causes an end effector 208 to extend from the instrument body 201 and also controls the positioning of the end effector 208 by operating a flexible joint 207. The flexible joint 207 can be bent directly by manipulation of the wire transmission linkages 202. Alternatively, a four-bar mechanical linkage can be incorporated into the surgical device 200 to amplify the force/torque applied to the end effector. FIG. 3 illustrates one example of such a mechanical linkage. The mechanism includes a first link 301, a second link 302, and the end effector 303. The four-bar linkage 304 adjusts the position of each link relative to the adjacent link. The wire transmission linkages 305 provide actuation of both of the four-bar linkages.

Instead of (or in addition to) adjusting the position of the end effector, the magnetic linkage between the actuation tool 100 and the surgical device 200 can be used to operate a variety of other tools that can be housed in instrument body 201 in other constructions of the surgical device 200. For example, the end effector 208 can include a surgical camera (with or without a steerable head), tissue retractors, cautery devices, surgical electrofrequency knives, laparoscopic graspers, and surgical pinching devices. In each of these alternative constructions, the tool positioned within the surgical device is either positioned or actuated by manipulation through the magnetic coupling with the actuation tool 100.

Figure 4:
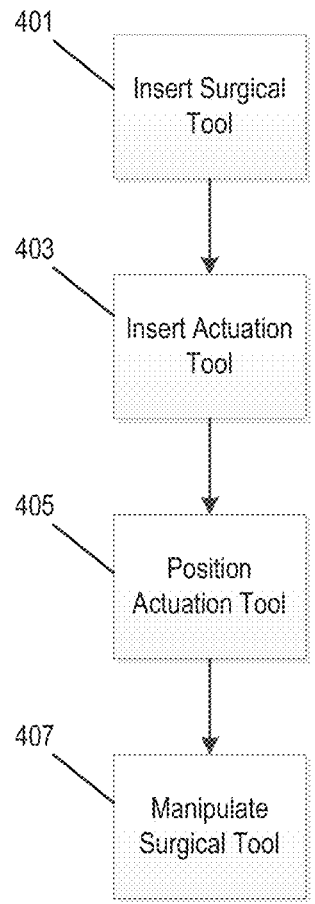
FIG. 4 is a flow-chart of a method for controlling the operation of the surgical device of FIG. 2 using the actuation tool of FIG. 1.
Figure 5A:
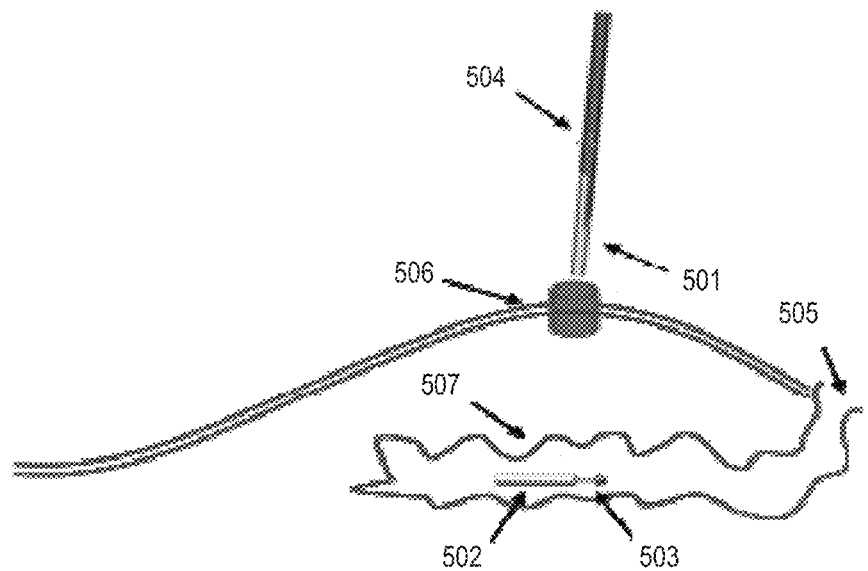
FIGS. 5A, 5B, and 5C are partially cross-sectional perspective views of the surgical device and the actuation tool during the method of FIG. 4.
Figure 5B:
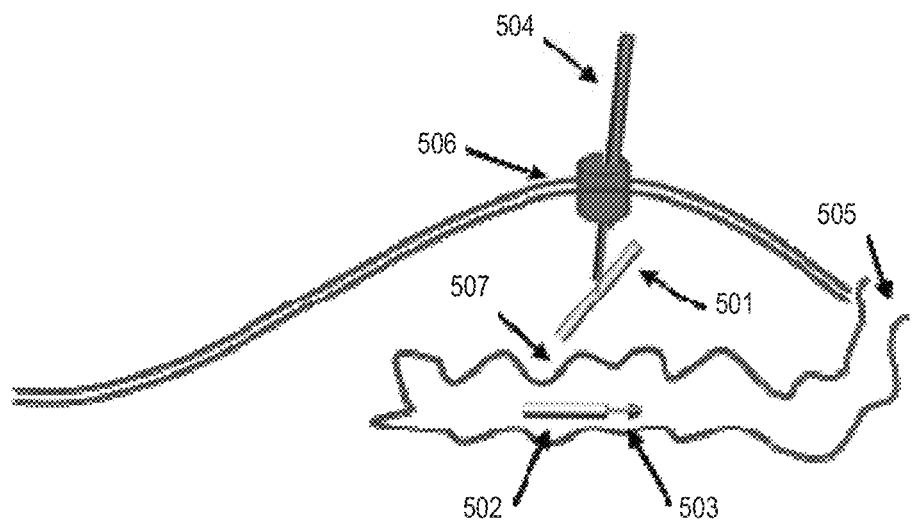

FIG. 4 illustrates a method of performing a surgical operation inside a body cavity using the actuation tool 100 and the surgical device 200 described above. First, the surgical tool is inserted into a body cavity (step 401). As illustrated in FIG. 5A, the surgical tool 502 is inserted through a natural orifice 505 such as, for example, the anus, the vagina, or the mouth of a patient. The distal end of the actuation tool 501 is inserted through a surgical access port 506 (e.g., through an abdominal wall incision) (step 403). When inserted, the handle 504 of the actuation tool 501 continues to extend to the exterior of the patient's body as illustrated in FIGS. 5A and 5B.

Figure 5C:
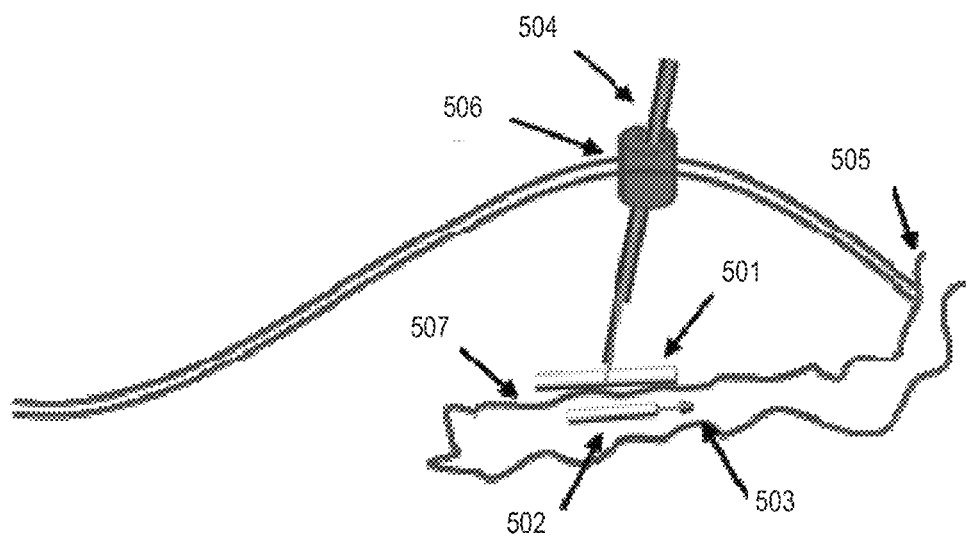

The distal end of the actuation tool 501 is then positioned near the exterior of the body cavity wall 507 (step 405). As shown in FIG. 5B, the rotational joint of the actuation tool 501 is manipulated to position all of the magnets within the distal end of the actuation tool 501 adjacent to the exterior of the body cavity wall. After the distal end of the actuation tool 501 is properly positioned near the exterior of the body cavity wall and a magnetic coupling is established between the actuation tool 501 and the surgical device 502, the actuation tool 501 is used to manipulate the operation of the surgical device 502 (step 407). As shown in FIG. 5C, the actuator tool 501 is positioned on the exterior surface of the body cavity wall while the surgical device 502 is positioned on the interior surface adjacent to the distal end of the actuation tool 501. This is done through magnetic coupling of the anchoring magnets as described above in reference to FIGS. 1 and 2. Once magnetically coupled, the operation of the end effector 503 (i.e., the camera, grasper, cautery tip, etc.) of the surgical tool is controller through the actuation tool 501.

Although the examples described above rely on magnetic coupling, other constructions may incorporate other types of non-physical mechanical couplings. Furthermore, although the examples above describe non-surgical insertion of the surgical device into a natural orifice, other constructions of the systems described above can be inserted through a surgical incision.

Thus, the invention provides, among other things, a systems and methods for controlling the operation of a surgical device positioned within a body cavity through coupling with an actuation tool positioned at the exterior of the body cavity wall. Various features and advantages of the invention are set forth in the following claims.

What is claimed is:

1. A method of actuating a medical device, the method comprising:

inserting a distal end of an actuation tool into a body of a patient through a surgical access port, wherein the actuation tool includes a handle that extends from the surgical access port;

positioning the distal end of the actuation tool proximal to a surface of an anatomical structure, wherein the medical device is positioned on an opposite side of the anatomical structure;

establishing a magnetic coupling between the distal end of the actuation tool and the medical device; and actuating a function of the medical device through the magnetic coupling with the actuation tool, wherein manipulating the medical device through the magnetic coupling with the actuation tool includes controlling linear movement of an actuator magnet in the actuation tool which causes a corresponding linear movement of a driven magnet in the medical device, wherein linear movement of the driven magnet causes a 4-bar linkage to tilt an end effector of the medical device relative to an instrument body housing of the medical device.

2. The method of claim 1, wherein the anatomical structure includes a wall of a body cavity and wherein the medical device is positioned within the body cavity.

3. The method of claim 2, wherein the medical device is inserted into the body cavity through a natural orifice.

4. The method of claim 1, wherein the medical device includes a surgical tool that is operated through the magnetic coupling with the actuation tool.

5. The method of claim 1, further comprising activating a rotational joint to cause an actuator body at the distal end of the actuation tool to rotate relative to the handle of the actuation tool after the distal end of the actuation tool has been inserted through the surgical access port.

6. A method of actuating a medical device, the method comprising:

inserting a distal end of an actuation tool into a body of a patient through a surgical access port, wherein the actuation tool includes a handle that extends from the surgical access port;

positioning the distal end of the actuation tool proximal to a surface of an anatomical structure, wherein the medical device is positioned on an opposite side of the anatomical structure;

establishing a magnetic coupling between the distal end of the actuation tool and the medical device; and actuating a function of the medical device through the magnetic coupling with the actuation tool, wherein establishing a magnetic coupling between the distal end of the actuation tool and the medical device includes coupling an anchor magnet of the actuation tool to an anchor magnet of the medical device and coupling an actuator magnet of the actuation tool with a driven magnet of the medical device, wherein the coupling of the anchor magnets prevents movement of a medical device housing relative to the actuation tool, and wherein the coupling of the actuator magnet to the driven magnet causes linear movement of the actuator magnet within the actuation tool to cause corresponding linear movement of the driven magnet within the medical device housing.

7. The method of claim 6, wherein the anatomical structure includes a wall of a body cavity and wherein the medical device is positioned within the body cavity.

8. The method of claim 6, wherein the medical device is inserted into the body cavity through a natural orifice.

9. The method of claim 6, wherein the medical device includes a surgical tool that is operated through the magnetic coupling with the actuation tool.

10. The method of claim 6, further comprising activating a rotational joint to cause an actuator body at the distal end of the actuation tool to rotate relative to the handle of the actuation tool after the distal end of the actuation tool has been inserted through the surgical access port.

11. A medical device actuation system comprising an actuation tool, the actuation tool including:

an actuation body including an anchor magnet and an actuation magnet, the anchor magnet being magnetically couplable to a corresponding anchor magnet of a medical device to prevent movement of the medical device relative to the actuation body of the actuation tool, and the actuation magnet being magnetically couplable to a corresponding driven magnet of the medical device such that, when coupled, linear movement of the actuation magnet causes a corresponding linear movement of the driven magnet of the medical device; and a substantially linear handle coupled to the actuation body such that the actuation body is insertable into a body of a patient through a minimally invasive surgical access port and positioned at an exterior surface of an anatomical structure, wherein the actuation tool further includes a rotational joint coupling the actuation body to the handle such that the actuation tool is rotatable from a first position to a second position, wherein, when the actuation tool is in the first position, a housing of the actuation tool containing the anchor magnet and the actuation magnet is substantially co-linear with the handle, and wherein, when the actuation tool is in the second position, the housing of the actuation tool containing the anchor magnet and the actuation magnet is positioned at an angle relative to the handle and positioned such that the anchor magnet and the actuation magnet are adjacent to the surface of the anatomical structure.

12. The medical device actuation system of claim 11, further comprising the medical device, wherein the medical device includes a surgical tool that is insertable into a body cavity through a natural orifice.

13. The medical device actuation system of claim 12, wherein the surgical tool includes a housing, the anchor magnet of the medical device, the driven magnet of the medical device, and an end effector that is coupled to the driven magnet such that movement of the driven magnet affects operation of the end effector.

14. The medical device actuation system of claim 13, wherein the surgical tool further includes a linkage segment, a first 4-bar linkage connecting the linkage segment to the housing, a second 4-bar linkage connecting the end effector to the linkage segment, and a wire transmission connecting the driven magnet to both the first 4-bar linkage and the second 4-bar linkage such that linear movement of the driven magnet causes the first 4-bar linkage to tilt the linkage segment relative to the housing and causes the second 4-bar linkage to tilt the end effector relative to the linkage segment.

15. A medical device actuation system comprising an actuation tool, the actuation tool including:

an actuation body including an anchor magnet and an actuation magnet,
- the anchor magnet being magnetically couplable to a corresponding anchor magnet of a medical device to prevent movement of the medical device relative to the actuation body of the actuation tool, and
- the actuation magnet being magnetically couplable to a corresponding driven magnet of the medical device such that, when coupled, linear movement of the actuation magnet causes a corresponding linear movement of the driven magnet of the medical device; and a substantially linear handle coupled to the actuation body such that the actuation body is insertable into a body of a patient through a minimally invasive surgical access port and positioned at an exterior surface of an anatomical structure, further comprising the medical device, wherein the medical device includes a surgical tool that is insertable into a body cavity through a natural orifice, wherein the surgical tool includes
- a housing,
- the anchor magnet of the medical device,
- the driven magnet of the medical device, and
- an end effector that is coupled to the driven magnet such that movement of the driven magnet affects operation of the end effector, wherein the surgical tool further includes a 4-bar linkage connecting the end effector to the housing and a wire transmission connecting the driven magnet to the 4-bar linkage such that linear movement of the driven magnet causes the 4-bar linkage to tilt the end effector relative to the housing.

16. The medical device actuation system of claim 15, wherein the surgical tool further includes a linkage segment, the 4-bar linkage comprising a first 4-bar linkage connecting the linkage segment to the housing, a second 4-bar linkage connecting the end effector to the linkage segment, and a wire transmission connecting the driven magnet to both the first 4-bar linkage and the second 4-bar linkage such that linear movement of the driven magnet causes the first 4-bar linkage to tilt the linkage segment relative to the housing and causes the second 4-bar linkage to tilt the end effector relative to the linkage segment.

17. A surgical device positioning system comprising:

a surgical device insertable into a body cavity through a natural orifice, the surgical device including an anchor magnet and a driven magnet coupled to an end effector device such that linear movement of the driven magnet affects the operation of the end effector device; and an actuation tool insertable through a surgical access port to position an actuation body adjacent to an exterior surface of a wall of the body cavity, the actuation body including
- an anchor magnet couplable to the anchor magnet of the surgical device through the wall of the body cavity to restrict movement of the surgical device relative to the actuation body,
- an actuation magnet couplable to the driven magnet of the surgical device through the wall of the body cavity to affect operation of the end effector device of the surgical device by causing linear movement of the driven magnet, and
- a housing, wherein the anchor magnet and the actuation magnet are positioned within the housing on a first axis, and the actuation tool further including
- a substantially linear positioning handle that extends from the surgical access port when the actuation body is positioned adjacent to the exterior surface of the wall of the body cavity, and
- a rotational joint coupling the actuation body to the positioning handle and configured to selectively move the actuation body from a first rotational position to a second rotational position, wherein, when in the first rotational position, the first axis of the actuation body housing is substantially co-linear with the positioning handle and, when in the second rotational position, the anchor magnet and the actuation magnet are positioned adjacent to the exterior surface of the wall of the body cavity.

* * * * *